US005455475A

United States Patent [19]
Josse et al.

[11] Patent Number: 5,455,475
[45] Date of Patent: Oct. 3, 1995

[54] PIEZOELECTRIC RESONANT SENSOR USING THE ACOUSTOELECTRIC EFFECT

[75] Inventors: Fabien J. Josse; Zack A. Shana, both of Milwaukee, Wis.

[73] Assignee: Marquette University, Milwaukee, Wis.

[21] Appl. No.: 146,386

[22] Filed: Nov. 1, 1993

[51] Int. Cl.$^6$ ............................. G01N 29/00; H01L 41/08
[52] U.S. Cl. ..................... 310/316; 310/322; 310/338; 73/54.25
[58] Field of Search ..................... 310/312, 316, 310/321–323, 338, 320; 73/24.02, 24.03, 28.05, 54.25–54.41, 61.45, 61.49

[56] References Cited

U.S. PATENT DOCUMENTS

| | | | |
|---|---|---|---|
| 2,483,829 | 10/1949 | Hershberger | 73/24.02 |
| 3,260,104 | 7/1966 | King | 73/24.02 |
| 3,561,253 | 2/1971 | Dorman | 73/24.02 |
| 3,879,992 | 4/1975 | Bartera | 310/319 |
| 4,236,893 | 12/1980 | Rice | 310/312 |
| 4,242,096 | 12/1980 | Oliveira et al. | 310/312 |
| 4,721,874 | 1/1988 | Emmert | 310/316 |
| 4,741,200 | 5/1988 | Hammerle | 73/54.25 |
| 4,870,313 | 9/1989 | Hirama et al. | 310/320 |
| 5,201,215 | 4/1993 | Granstaff et al. | 73/54.41 |
| 5,211,053 | 5/1993 | Muramatsu | 73/64.42 |
| 5,235,238 | 8/1993 | Nomura et al. | 310/349 |
| 5,283,037 | 2/1994 | Baer et al. | 310/312 |

OTHER PUBLICATIONS

"Quartz Crystal Resonators as Sensors in Liquids Using the Acoustoelecric Effect", Shana & Tossi, Anal Chem, 1994, 66, 1955–1964.
Acoustoionic Interaction of SH Surface Waves with Dilute Ionic Solutions; Josse and Shana, 1991 IEEE, vol. 38, No. 3, May, 1991 pp. 297–304.
Quartz Resonator as Sensor for Viscous/Conductive Liquids; Josse et al.; "Electronics Letters", Oct. 12, 1989, vol. 25, No. 21, pp. 146–1447.
LiNbO$_3$ Acoustic Plate Mode Sensor for Dilute Ionic Solutions; Josse et al.; "Electronics Letters", Jun. 21, 1990, vol. 26, No. 13, pp. 834–835.
Analysis of Piezoelectric Bulk–Acoustic–Wave Resonators as Detectors in Viscous Conductive Liquids; Josse et al.; 1990 IEEE, vol. 37, No. 5, Sep., 1990, pp. 359–368.
Electrical Surface Perturbation of a Piezoelectric Acoustic Plate Mode by a Conductive Liquid Loading; Josse and Shana; 1992 IEEE, vol. 39, No. 4, Jul., 1992, pp. 512–518.
Theory and Applications of Quartz Resonators as Sensors for Viscous Conductive Liquids; Shana et al.; IEEE Ultrasonics Symposium, 1989, pp. 567–571.
Probing of Strong and Weak Electrolytes with Acoustic Wave Fields; Dahint et al.; "Sensors and Actuators" 1992, pp. 155–162.
On the Use of ZX–LiNbO$_3$ Acoustic Plate Mode Devices as Detectors for Dilute Electrolytes; "Sensors and Actuators", 1992 pp. 97–112 Josse et al.
Acoustic Plate Waves for Measurements of Electrical Properties of Liquids; "Microchemical Journal", vol. 43, pp. 155–164 (1991) Josse et al.

Primary Examiner—Thomas M. Dougherty
Attorney, Agent, or Firm—Albert W. Watkins

[57] ABSTRACT

An AT cut quartz crystal resonator has an unbalanced electrode geometry to induce a particularly strong electrical field in a surface of the resonator adjacent a medium. The electrical field will interact with ions and dipoles in the medium and may be used to accurately and repeatably measure the electrical characteristics of the medium. Specific examples are provided illustrating the use of a sensor designed in accord with the invention in sensing dilute electrolytes, and other applications are contemplated.

12 Claims, 7 Drawing Sheets

PIEZOELECTRIC RESONANT SENSOR USING THE ACOUSTOELECTRIC EFFECT

BACKGROUND OF THE INVENTION

1. Field of the Invention

This invention pertains generally to electrical equipment for measuring and testing, and more specifically to the design of piezoelectric resonators and systems to utilize the acoustoelectric effect to measure electrical properties of a medium.

2. Description of the Related Art

Piezoelectric materials are materials which generate electricity when subjected to mechanical stress and, conversely, generate mechanical stress when a voltage is applied. There are many materials which are piezoelectric. These piezoelectric materials have found application in many diverse technologies, ranging from mechanical actuators and gas igniters to very precise timekeeping.

The uses for piezoelectric devices derive from the conversion of electricity to motion or vibration and, often, the reconversion of that motion back into electricity. For example, a precision clock oscillator will utilize a quartz crystal of very precise dimension and mass. Electrodes are formed on the surface of the crystal, and an electric field is applied. This stimulates a mechanical stress in the quartz.

If the applied voltage changes at or near the resonant frequency of the crystal, a sustained vibration may be generated in the quartz. At the resonant frequency of the quartz, which may be determined by cut angle, thickness, length, width and mass, an electrically alternating current may pass through the crystal with very little loss. Outside of this frequency, larger losses will occur in the alternating current as it is passed through the crystal.

The Q of a crystal is a measure of how narrow a band of frequencies is passed by the crystal with minimum attenuation relative to the resonant frequency of the crystal. Often the Q of a piezoelectric material will determine the useful application. For example, very low Q materials are capable of converting wide frequency bands to and from mechanical energy. These materials are often used as sonic transducers in applications such as in microphones or speakers. The low Q allows for many tones to be produced.

Other applications demand a great deal of precision, such as timekeeping. For these applications, a material with a very high Q is preferred, since only a very narrow band of frequencies may then be passed through the piezoelectric material. In these precision applications, the piezoelectric material is usually associated with an electronic oscillator circuit, where the oscillator circuit will be caused to oscillate at the resonant frequency of the piezoelectric material.

With modern manufacturing methods, precision crystals of quartz or similar very high Q material may be made to oscillate at a frequency which is accurate to within a few parts per million. As noted above, this frequency is dependent upon the type of material, mass and dimensions of the crystal resonator. During the production of the quartz resonators, layers of conductive electrode material are typically deposited to a precision of only a few atomic layers, since the resonators will be sensitive to changes in mass as small as this.

The characteristic sensitivity of high Q piezoelectric materials to changes in mass has led industry to a number of diverse applications. For example, a quartz resonator may be coated with an absorbent which is selective to a particular compound. The amount or concentration of that compound may be determined just by monitoring the change in resonant frequency of the quartz as the compound is absorbed. As more of the compound is absorbed, the mass of the vibrating structure is increased.

Similarly, amounts of material deposited in a vacuum deposition chamber may be very accurately monitored by including a quartz resonator in the deposition area. As more material is deposited upon a surface of the quartz resonator, the frequency of the quartz will also change, thereby indicating with great precision the thickness of the deposited layer.

Many other similar applications for precision resonators have been devised. For the purposes of this disclosure, these applications will be referred to herein as crystal microbalances. That is, the addition or subtraction of mass in the region of vibration of the piezoelectric material results in a change in the resonant frequency of vibration. Common applications for crystal microbalances include gas sensing, mass detection for very small masses, film thickness monitoring, microbe and similar biological sensing, and frequency control. Other more recent applications include viscosity and density detectors.

The use of mass or viscosity sensing limits the applicability of the very sensitive quartz resonator to those situations where a change of mass, density or viscosity may be expected or generated. The present inventors have sought to overcome the limitations of the prior art through the use of a new type of sensor which utilizes the acoustoelectric effect that is characteristic of piezoelectric materials. For the purposes of this disclosure, the acoustoelectric effect will be defined as an electrical interaction between a medium and a vibrating piezoelectric material, wherein the medium acts to electrically load the piezoelectric material proportionate to one or more electrical characteristics of the medium.

The acoustoelectric effect as defined herein was introduced by the present inventors and others in a paper entitled "Theory and Applications of Quartz Resonators as Sensors for Viscous Conductive Liquids," incorporated herein by reference. The sensor which formed the topic of that paper was neither reproducible nor sufficiently sensitive to form the resonator structure for a commercial sensor. Furthermore, the theory in that paper ignored the existence of the metal electrode in deriving the acoustoelectric effect.

Additional structures were attempted which addressed the issues of sensitivity and reproducibility. These sensors utilized a lithium niobate piezoelectric material of high piezoelectric coupling in an acoustic plate mode arrangement. The acoustic plate mode device propagates the wave from a first electrode, commonly referred to as an interdigital transducer or IDT, to a second IDT. The amount of acoustoelectric interaction present at the surface of the acoustic plate mode device affects the propagating properties of the wave through the device. By monitoring the time delay or phase change and attenuation, it is possible to determine through the acoustoelectric effect various electrical properties of the medium. For example, liquid properties such as conductivity, ion concentration and dielectric constant can be monitored with high sensitivity.

However, lithium niobate is a relatively expensive material which restricts the applicability of the device to those applications which will tolerate the increased cost. Moreover, lithium niobate is extremely sensitive to changes in ambient temperature. Although the high electromechanical coupling coefficient of lithium niobate allows sufficient sensitivity, the acoustic plate mode device utilizes the surface acoustic wave device structure which requires a more elaborate oscillator circuit. Acoustic plate mode quartz devices constructed similarly were found not to have sufficient sensitivity.

The present invention seeks to overcome the limitations of the prior art both in terms of cost and reproducibility. The present invention thereby provides a sensor which may be affordably mass produced while at the same time providing great sensitivity and reproducibility.

SUMMARY OF THE INVENTION

A sensor capable of sensing changes in electrical properties of a medium in a precise and reproducible way includes a piezoelectric material of high Q, for example quartz. The material and a resulting resonator are designed to maximize acoustoelectric interaction with the medium on at least one surface. Together with an oscillator circuit the material resonates at a frequency relatively higher than the rate at which ions in the medium can form a significant charge concentration gradient. The resonator is electrically loaded by ions and dipoles in the medium, resulting in a change in parallel resonant frequency depending upon the electrical characteristics of the ions and dipoles. The extent of the electrical loading, or resulting frequency shift, is used to determine the electrical properties of the medium.

A method for measuring an electrical property of a medium includes the steps of determining a resonant frequency of oscillation at some reference, exposing a transition unelectroded region with a relatively high field at a surface of a piezoelectric resonator to the medium, comparing the resonant frequency of the piezoelectric resonator to the frequency of the reference, and calculating the characteristic of the medium based upon the frequency difference.

DESCRIPTION OF THE PREFERRED EMBODIMENT

The preferred embodiment of the present invention incorporates a quartz crystal AT cut resonator 11 or 21. For the purposes of this disclosure, a resonator is defined as a device within which standing waves are generated and maintained at some resonant frequency. Prior art acoustic plate mode devices do not generate standing waves and are not used as resonant structures in accord with this disclosure. A prior art AT cut crystal resonator 1 is illustrated from front and back views in FIGS. 1 and 2 respectively, and from flow cell installed cross section taken along section line 12. The top and bottom of the crystals has been reversed, to maintain left and right orientation in the front and back views. In other words, lead patterns 4 and 6 are not in overlapping arrangement, but are 180 degrees in opposition, as shown in the figures. The orientation of FIGS. 3–6 is similar.

Figure 1:
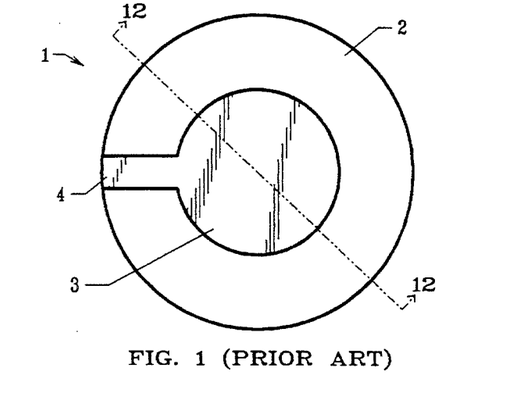
FIGS. 1 and 2 illustrate the top and bottom surfaces of a disc shaped prior art crystal resonator.

These figures show the AT cut quartz 2, electrically conductive lead pattern 4 and grounded electrically conductive electrode 3 in FIG. 1. Active electrode 5 is shown with crystal 2 and electrically conductive lead 6 in FIG. 2. In the prior art, crystals were generally designed to have grounded electrode 3 and active electrode 5 of roughly equal diameter.

Figure 2:
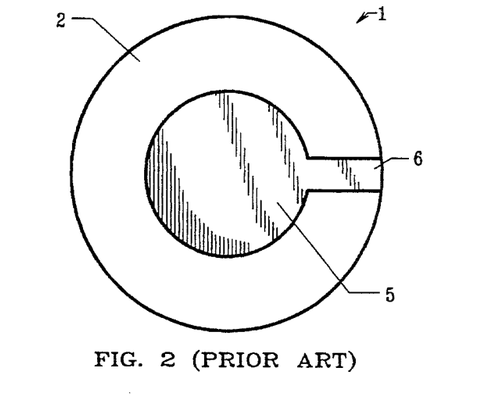
Figure 3:
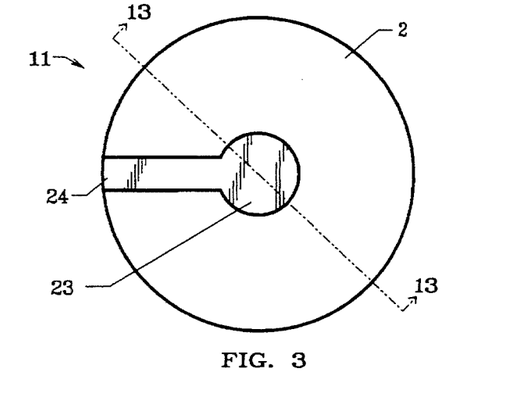
FIGS. 3 and 4 illustrate the top and bottom surfaces of a disc shaped crystal resonator in accord with the preferred embodiment of the present invention.
Figure 4:
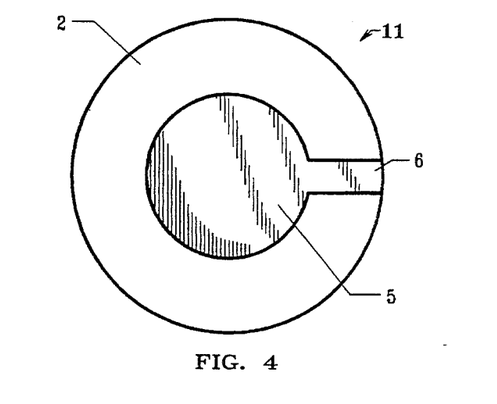
Figure 13:
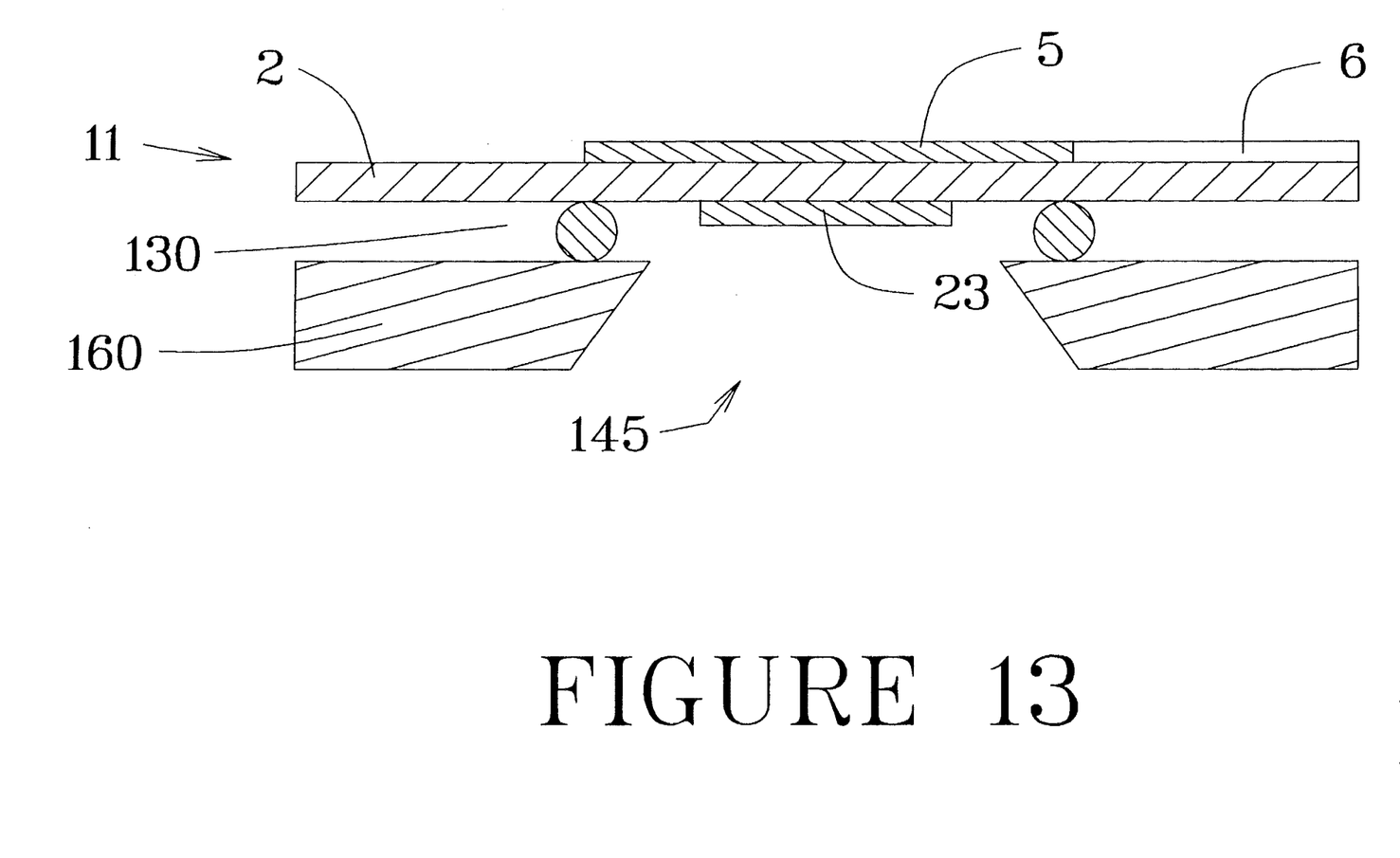
FIG. 13 illustrates the preferred embodiment crystal resonator attached to the flow cell of FIG. 7 by cross section taken along section line 13 of FIG. 3.

FIGS. 3, 4, and 13 illustrate the preferred embodiment resonator 11 from top, bottom, and section views respectively, wherein the active electrode 5 and lead 6 are of the same geometry as in prior art FIG. 2. However, the grounded electrode 23 is of smaller diameter than electrodes 3 or 5. In the preferred embodiment, electrode 23 is four-sevenths the diameter of electrode 5.

A trade-off in choosing a size for electrode 23 must be made. As electrode 23 is made smaller, more unelectroded surface area of quartz 2 in which the excitation electrodes (for example 23 and 5) do not overlap is made available. It is this surface area, as will be described later, that interacts with the medium to be sensed. Greater interaction is obtained with progressively smaller electrodes. However, a minimum size will be reached for electrode 23 where the limit is in the size required to excite crystal 2 sufficiently to ensure oscillation. One of skill in the art will recognize the number of parameters that influence whether a crystal such as crystal 2 will oscillate. Adjustments are known in the art that may be made to the oscillator 200 (shown in FIG. 10) and resonator 11 to attempt to gain the best combination of features.

Figure 5:
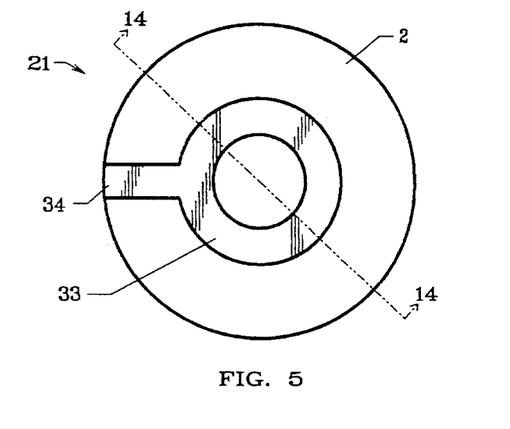
FIGS. 5 and 6 illustrate the top and bottom surfaces of an alternative embodiment of a disc shaped crystal resonator.
Figure 6:
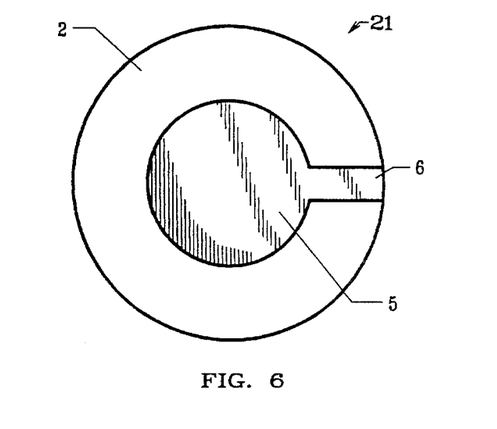
Figure 14:
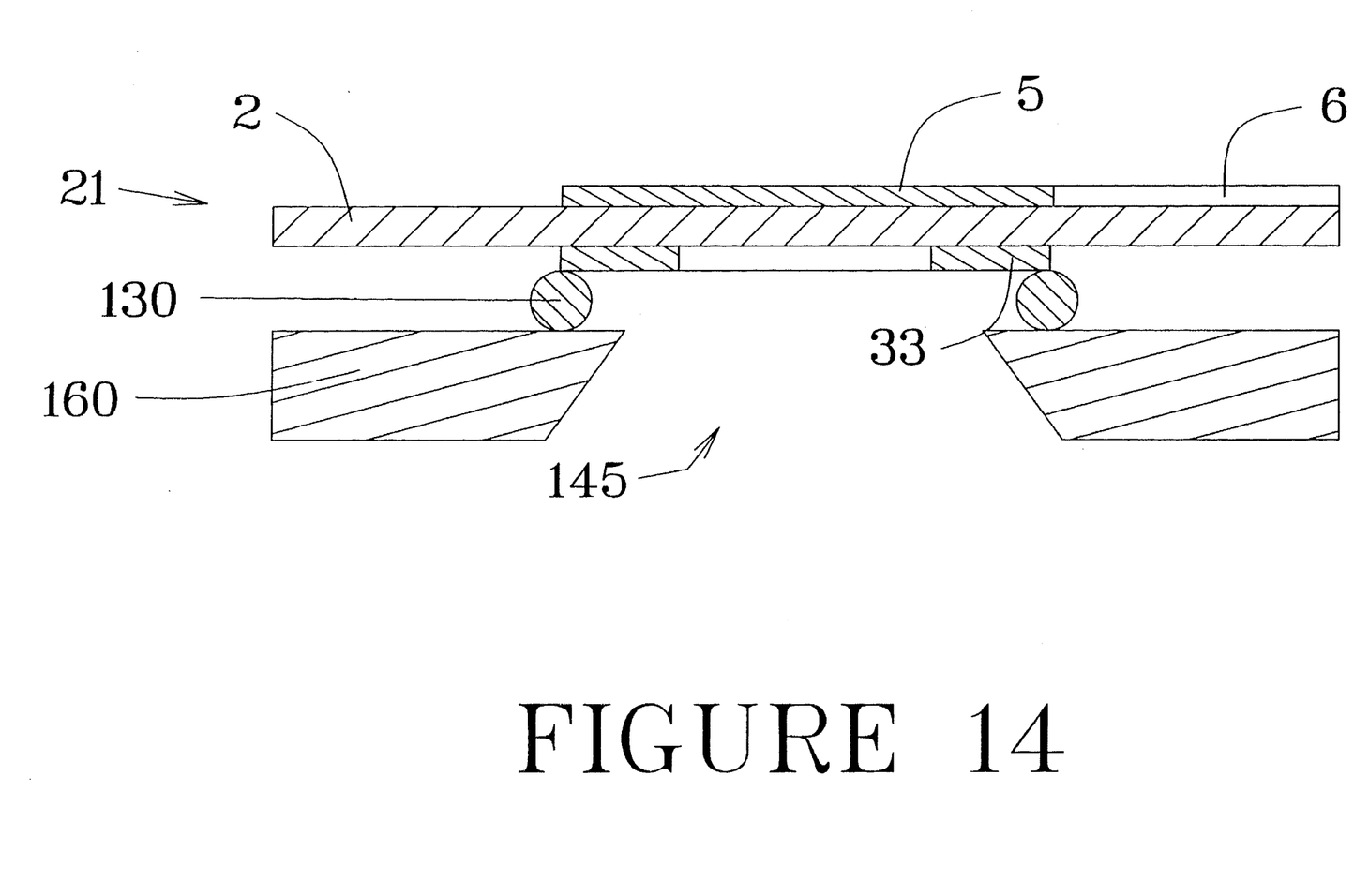
FIG. 14 illustrates an alternative embodiment crystal resonator attached to the flow cell of FIG. 7 by cross section taken along section line 14 of FIG. 5.

An alternative embodiment is illustrated in FIGS. 5, 6 and 14. Once again, FIG. 6 illustrates a known prior art electrode 5. Noteworthy is the fact that, as in the case of FIGS. 3 and 4, the electrode 5 may be proportionally very large, to the point of covering the entire crystal 2 surface upon which electrode 5 resides. Alternatively, the electrode may be much smaller, though a smaller electrode would usually only be the case in very high frequency resonators for reasons apparent to those skilled in the art.

However, FIG. 5 illustrates a very different ring shaped electrode 33 interconnected through electrode 34. Ring electrode 33 leaves exposed a center portion thereof of quartz 2.

Figure 7:
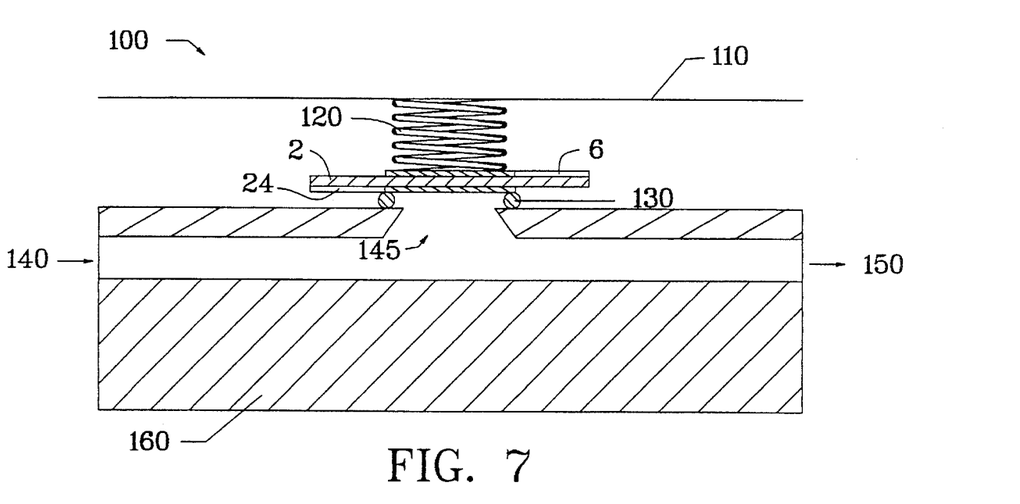
FIG. 7 illustrates a first embodiment of a flow cell adapted for use in the preferred embodiment of the invention.

FIG. 7 illustrates a flow cell 100 via a longitudinal cross section to expose the fluid flow path. Flow cell 100 has thereon a cover 110, which is purely a structural member designed to support spring 120 and maintain opposing forces thereto. Where cover 110 and spring 120 are conductive, it is possible to use these structures in combination with electrode 5 to serve as a signal carrying connection. Spring 120 can also be nylon, in which case other appropriate signal connections must be made. Crystal 2 is pressed against O-ring 130 by force applied through spring 120 to thereby form a fluid tight seal with cell structure 160. Cell structure 160 has a fluid inlet 140 which connects to delivery chamber 145. Delivery chamber 145 is closed on one surface by resonator 11, thereby interacting electrode 23 and quartz 2 with the fluid retained therein. The fluid passes from chamber 145 through outlet 150 into components which will be discussed in further detail with reference to FIG. 9.

Figure 8:
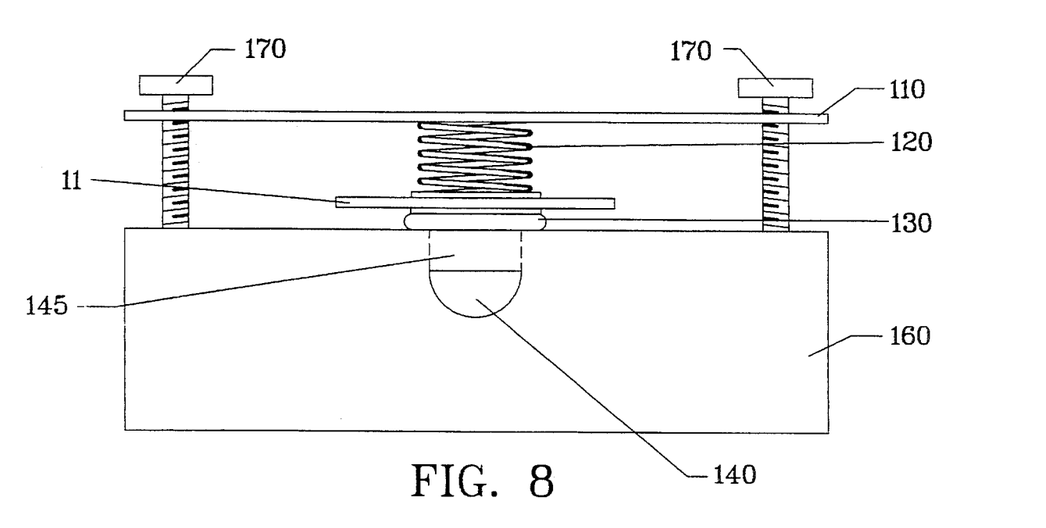
FIG. 8 illustrates an alternative flow cell adapted for use in the preferred embodiment.

FIG. 8 illustrates structure to positionally retain cover 110 relative to cell 160 in the form of two threaded rods 170. These rods have threads which engage with mating threads in plate 110. Rotation of rods 170 will cause a motion of cover 110 towards or away from cell 160. All other components of FIG. 8 are similar to and like numbered to those of FIG. 7.

Figure 9:
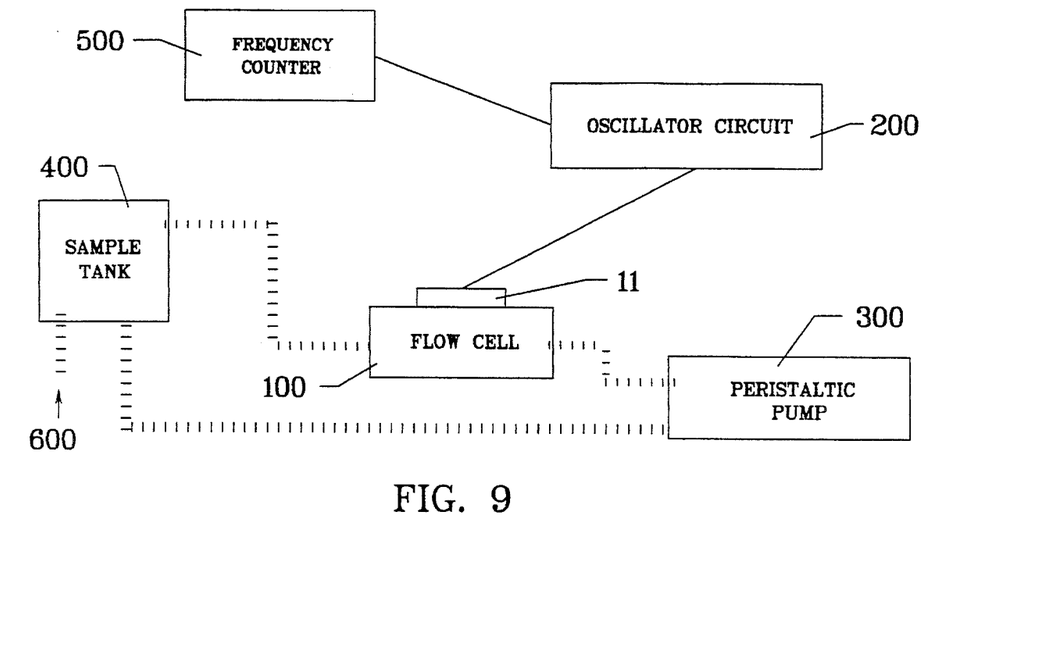
FIG. 9 illustrates a sensing system with fluid flow in accord with the preferred embodiment of the invention.

FIG. 9 illustrates by block diagram the fluid flow through the system. Oscillator circuit 200 (illustrated in more detail in FIG. 10) is used to electrically drive resonator 11. Resonator 11 is firmly held in place within flow cell 100 as shown for example in FIG. 8. The frequency of oscillator circuit 200 is monitored by frequency counter 500. Peristaltic pump 300 is used to circulate the fluid to be sensed from sample tank 400 through pump 300, through flow cell 100, and back to sample tank 400 in a recirculating manner. Fluid may be added or drained as required through drain tube 600.

Figure 10:
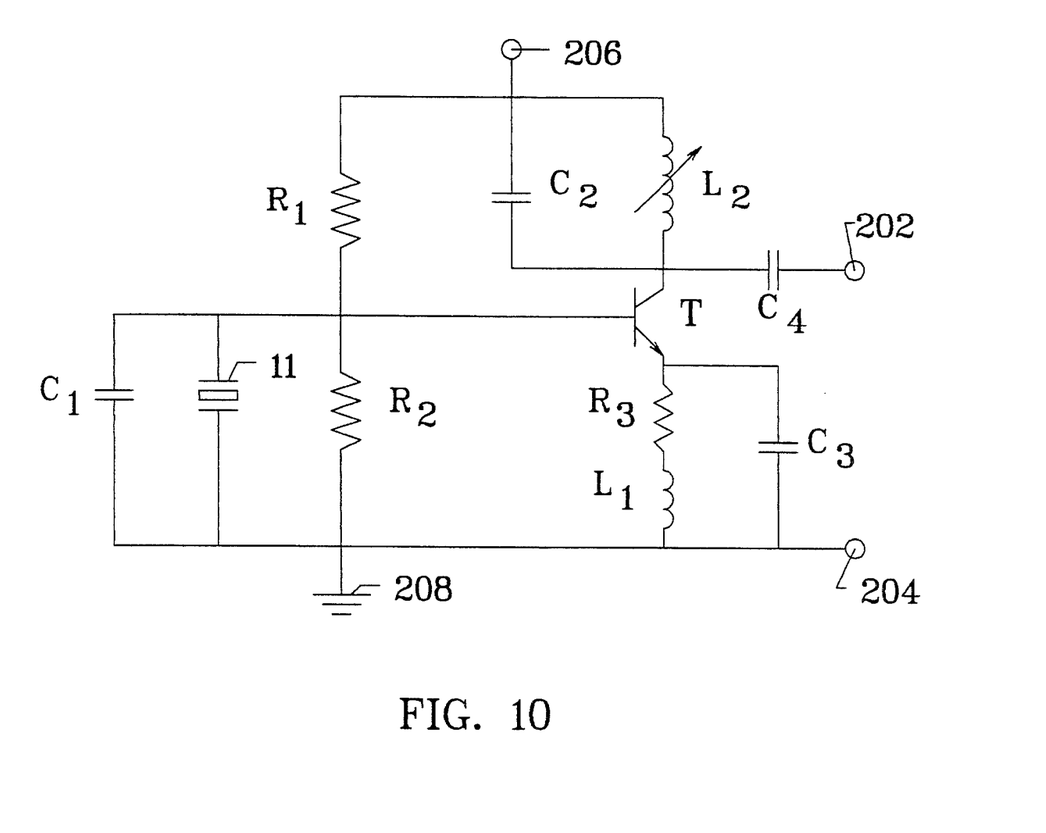
FIG. 10 illustrates in electrical schematic form the oscillator circuit for use with the preferred embodiment.

FIG. 10 illustrates the oscillator circuit in more detail. As shown, the oscillator circuit is a strongly driven tuned input tuned output oscillator. The resonator 11 is connected as the input tank, with the grounded electrode lead 24 connected to ground 208. The active electrode lead 6 is connected to the base of the transistor T. A DC source is applied through terminal 206 and ground 208. Oscillator 200 may be properly tuned by adjustment of L2, while frequency counter 500 may be connected across output terminals 202 and 204. Those skilled in the art will understand that there are a variety of suitable oscillator circuits and that this is just one exemplary circuit.

Figure 11:
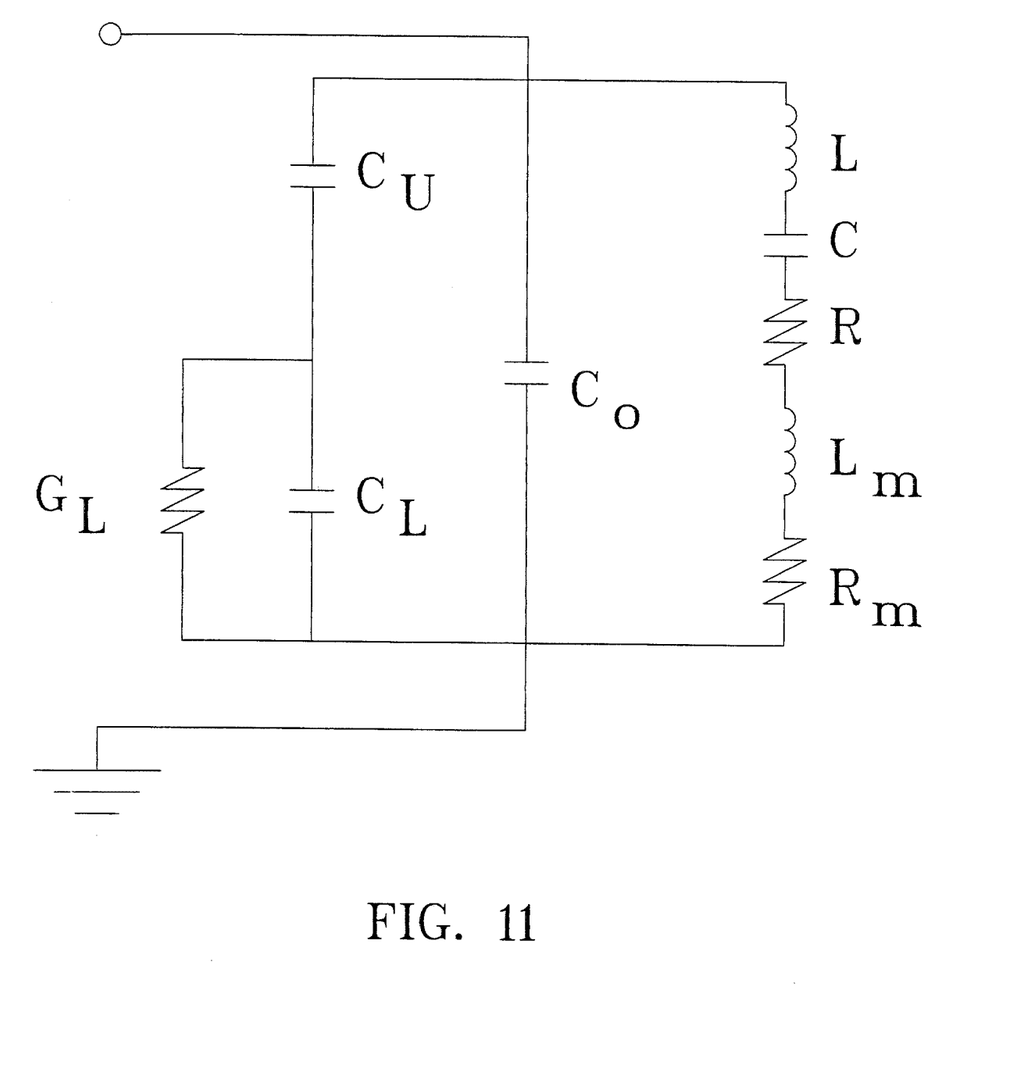
FIG. 11 illustrates the electrical equivalent circuit of the loaded piezoelectric resonator of the present invention.
Figure 12:
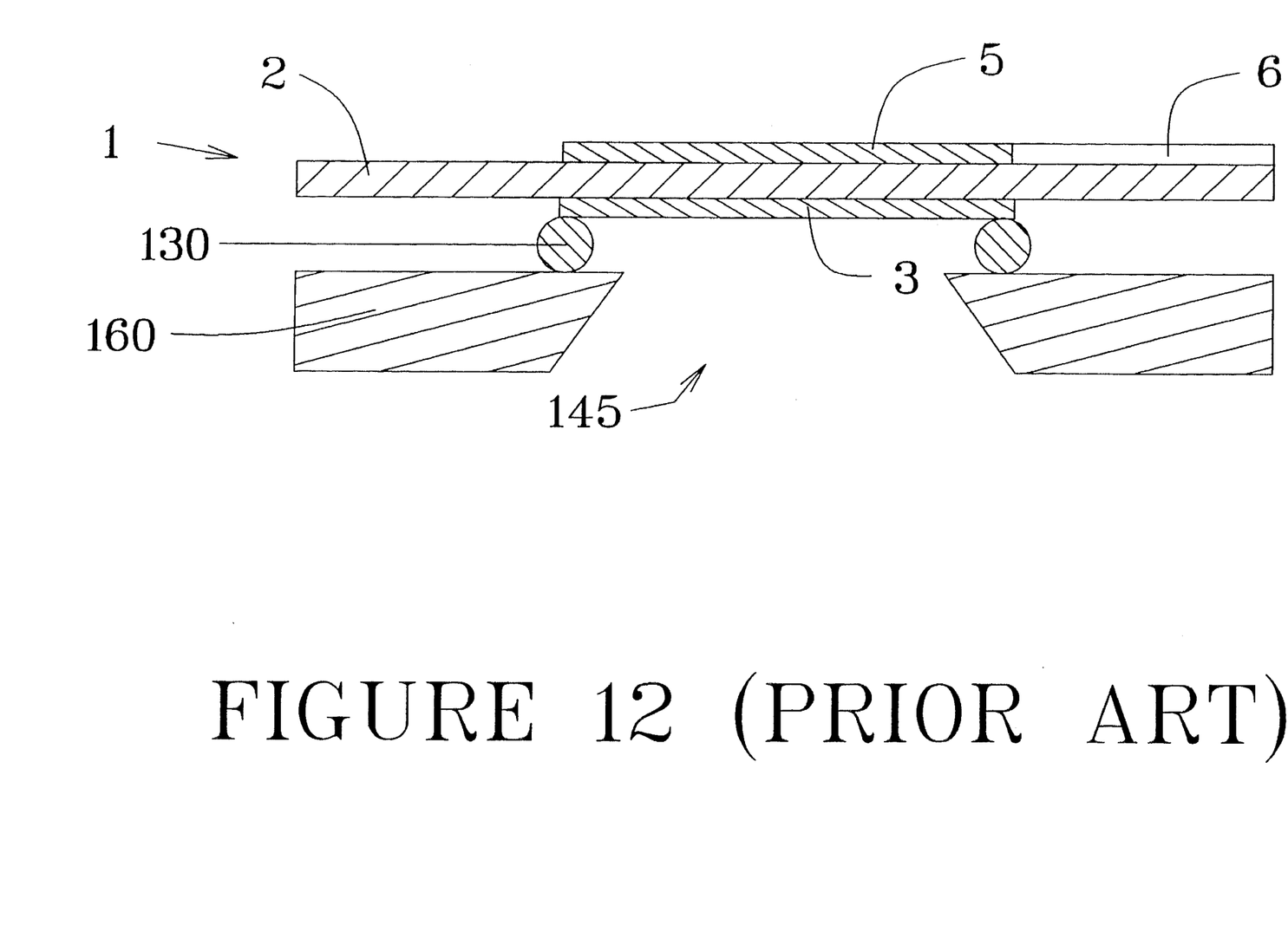
FIG. 12 illustrates the prior art crystal resonator attached to the flow cell of FIG. 7 by cross section taken along section line 12 of FIG. 1.

FIG. 11 illustrates the equivalent circuit for the loaded resonator 11 or 21. In this circuit, the inductance L and capacitance C are proportional to the mass and compliance of the piezoelectric crystal, respectively. The resistance R is associated with the loss resistance of the crystal mechanical energy. The resistance $R_m$, and inductance $L_m$ associated with the mechanical loading of the liquid, are related to the viscous losses and the fluid inertia, respectively. The electrical arm of the circuit consists of the static capacitance $C_0$ in parallel with another capacitance $C_u$, $C_u$ itself in series with the liquid impedance $Z_L = 1/Y_L$ where $Y_L = G_L + j\omega C_L$.

$$C_o = (A/d)\epsilon_s$$

where $\epsilon_s$ is the quartz dielectric constant, $A = \pi r_1^2$ is the grounded electrode 23 surface area and $d = \lambda/2$ ($\lambda$=wavelength) is the quartz plate thickness.

$$C_u = (A_1/d)\epsilon_s$$

where $A_1 = \pi(r_2^2 - r_1^2)$ is the intermediate unelectroded surface area in contact with the solution, where $r_2$ is the radius of active electrode 5.

$$C_L = A_1/l\epsilon_L$$

where $\epsilon_L$ is the liquid dielectric constant and $l$ characterizes the penetration depth of the field in the liquid from the unelectroded surface to the grounded electrode. Similarly $G_L$ is given by $\sigma A_1/l$ where $\sigma$ is the liquid conductivity.

An analysis of the above circuit indicates that the various critical frequencies depend on the mechanical quality factor of the crystal and the capacitance ratio $C_o'/C$ where $C_o'$ is given by $C_o' = C_o + C_1$ with $$C_1 = \frac{C_u[G_L^2 + \omega^2 C_L(C_L + C_u)]}{G_L + \omega^2(C_L + C_u)^2} \quad (1)$$

Of all the critical frequencies, only the series resonance frequency, $f_s$, is invariant with change in the electrical loading. The remaining frequencies depend on the values of $C_o'$. One of these frequencies, the parallel resonant frequency at which the resonator 11 under the electrolyte loading oscillates is approximately given by $$\omega_L \approx \frac{1}{\sqrt{L'C}}\left(1 + \frac{C}{2C_0'}\right) \quad (2)$$

where $L' = L + L_m$.

Because measurements in the preferred embodiment were made relative to a control liquid (in the examples that follow pure water was used to compare to dilute salt solutions), the frequency change due to the addition of the solute is obtained as $$\frac{\Delta f}{f} = \frac{\omega_L - \omega_W}{\omega_W} \quad (3)$$

where the parallel resonant frequency at which resonator 11 under distilled water loading oscillates, $\omega_W$, is calculated using Eq.(2), but with $C_o' = C_0 + C_2$ and $C_2$ given by Eq.(1) with $G_L = 0$ since $\sigma \approx 0$ for pure water. Furthermore, since the density and viscosity of the dilute conductive solution are basically the same as those of pure solvent, $$\left(\frac{1}{\sqrt{L'C_{solvent}}}\right) \approx \left(\frac{1}{\sqrt{L'C_{solution}}}\right) \quad (4)$$

Thus, Eq.(3) for the relative frequency change is reduced to $$\frac{\Delta f}{f} = \frac{C}{2}\left(\frac{1}{C_0 + C_1} - \frac{1}{C_0 + C_2}\right) \quad (5)$$

$$\approx \frac{1}{2}\frac{C}{C_0}\left(\frac{C_2 - C_1}{C_0 + C_u}\right)$$

Substituting for $C = 8K^2 C_0/\pi^2$ ($K^2$=electromechanical coupling coefficient), and $C_1$ and $C_2$ yield $$\frac{\Delta f}{f} = \frac{1}{2} \left( \frac{8K^2}{\pi^2} \right) \left( \frac{A_1}{A} \right) \left[ \frac{\left(\frac{l}{d}\right) \epsilon_s}{\left(\frac{l}{d}\right) s + \epsilon_L} \right] \left[ \frac{\sigma^2}{\sigma^2 + \omega^2 \left(\frac{l}{d} \epsilon_s + L\right)^2} \right] \quad (6)$$

Note that the expression for the relative change in frequency is analogous to that found for acoustic plate mode and other acoustic wave devices whose surface is in contact in a conductive liquid. However, Eq.(6) includes two modifying factors, $A_1/A$ and $l/d$ for the substrate dielectric constant. This expression coincides with experimental data generated to date. Note that as the radius $r_1$ of the grounded electrode 23 approaches that of the radius $r_2$ of active electrode 5, $A_1$, hence $\Delta f$, tends to zero. Any measured frequency shift for the prior art resonator 1 of FIGS. 1 and 2 can only be attributed to fringing fields. As noted in the discussions of the prior art, this varies depending upon several factors including the O-ring 130 diameter, and the concentricity of the grounded electrode 3 and active electrode 5. As a result, the prior art device of FIGS. 1 and 2 is not reproducible nor reliable for sensing and measuring based upon the acoustoelectric effect.

By modifying the grounded electrode 3 geometry of resonator 1 to resemble electrode 23 of resonator 11 or electrode 33 of resonator 21, a transition region is created. The transition region exists between the trapped energy region (fully electroded region) and the region with an evanescent wave, that is, the unelectroded region of prior art resonator 1. In this transition zone in which the excitation electrodes (for example electrodes 23 and 5) do not overlap but would have in prior art resonator 1, a relatively strong field is created. This field can interact with the adjacent conductive solution, resulting in a relatively strong change in the parallel resonance conditions. The fringing field created by resonator 1 of prior art FIGS. 1 and 2 has been calculated by the inventors to be about 20% of the maximum amplitude of the field found near the center of the electrodes. The transition field referred to herein is of amplitude generally several times the amplitude of the fringing field. Further, the fringing field decays very rapidly as the distance from the electrode area increases, where the decay rate of the transition field is not as great.

The equivalent circuit of FIG. 11 is a general circuit from which all other cases of a piezoelectric resonator in contact with a given fluid can be analyzed. Design of an appropriate oscillator circuit is then well within the ordinary skill in the art to measure the fluid parameter of interest.

EXAMPLES

A resonator was constructed in accord with the preferred embodiment of FIGS. 3 and 4. The resonator was an 11 Mhz AT cut quartz crystal having a grounded electrode 23 of 4 millimeter diameter and an active electrode 5 of 7 millimeter diameter. The resonator was assembled to a fluid cell as illustrated in FIGS. 7 and 8, and connected to an oscillator and fluid delivery system as illustrated in FIGS. 9 and 10. The oscillator circuit was properly tuned and the output voltage was monitored for a period of time to insure stability.

Distilled water was first added to the flow system and a frequency drop of about 5 Khz was observed. Various amounts of concentrated conductive solutions were added to sample tank 400 to produce different dilutions of electrolyte. The pump was turned off and the solution added and mixed in the tank before the pump was turned on again. The frequency drop due to the addition of each aliquot was then recorded after adequate time to insure complete mixing and system stabilization. All work was done at constant temperature.

The resonators 11 and 21 shifted in frequency by as much as 2 Khz, depending upon concentration of electrolyte. The results were reproducible within a few percent. The prior art sensor 1 generated a less than 300 Hz frequency shift when similarly tested, and the results were not reproducible.

While the foregoing details what is felt to be the preferred embodiment of the invention, no material limitations to the scope of the claimed invention is intended. Further, features and design alternatives that would be obvious to one of ordinary skill in the art are considered to be incorporated herein. For example, the preferred embodiment is illustrated as an AT cut quartz crystal. One of ordinary skill in the art will understand that there are many other resonator structures and piezoelectric materials which might perform in this application with similar results, provided the teachings of the invention are incorporated therein.

Further, the invention is not limited to the example of measuring dilute conductive aqueous electrolytes. The inventors have demonstrated applicability to a number of fluid media, and recognize that industrial applications will include such diverse areas as quantification of ionic solutes and industrial process water, continuous monitoring and control of chemical processes, quantification of dielectric properties and study of thin films of materials whose change in electrical properties will be detectable within the range of these devices.

This sensor is capable of monitoring any chemical, physical or biological process in which changes in the electrical properties occur during the process. For example, the diffusion of a gas into a thin polymer layer may result in a change in the dielectric constant of the polymer. In such cases, the acoustoelectric interaction between the sensor and the swelling polymer can be used to monitor the diffusion process.

Note that appropriate circuits can be designed to also monitor any possible change in mechanical acoustic load. The mechanical properties can be monitored by using the same resonator's series resonance frequency, which, as noted earlier, is not sensitive to electrical properties. This might be accomplished, for example, by switching in an oscillator in accord with the preferred embodiment to first measure the combined acoustoelectric and mechanical properties, and then switching out the oscillator of the preferred embodiment in favor of one using the series resonance of the crystal. The mechanical characteristics may then be subtracted from the first measurement, thereby yielding only the acoustoelectric effect. The scope of the invention is set forth and particularly described in the claims hereinbelow.

We claim:

1. A piezoelectric resonant sensor utilizing the acoustoelectric effect to accurately and reproducibly measure a change of electrical properties of a medium comprising:

a piezoelectric material having a first surface acoustoelectrically coupled to said medium;

a source of electrical energy;

a first excitation electrode and a second excitation electrode, said first and said second electrodes each having a primarily active electrode region electrically coupled to said source of electrical energy and said piezoelectric material to establish a resonant frequency therein;

said first electrode generating an active area in said first surface of said resonant sensor partially but incompletely overlapping with an active area in said first surface generated by electrical coupling of said second electrode with said second surface so as to create a transition region with an accentuated electric field in said piezoelectric material at said first surface and thereby reproducibly acoustoelectrically couple said first surface to said medium.

2. The piezoelectric resonant sensor of claim 1 wherein said piezoelectric material comprises quartz.

3. The piezoelectric resonant sensor of claim 1 wherein said first and second electrodes have an active geometry which is generally circular, said first electrode circular active geometry of smaller diameter than said second electrode circular active geometry.

4. The piezoelectric resonant sensor of claim 3 wherein said piezoelectric material comprises quartz.

5. The piezoelectric resonant sensor of claim 4 wherein said quartz piezoelectric material is AT cut.

6. The piezoelectric resonant sensor of claim 5 wherein said first electrode circular active geometry is four-sevenths the diameter of said second electrode circular active geometry.

7. A method of accurately and reproducibly measuring a change of electrical properties of a medium comprising the steps of:

measuring a frequency of oscillation of a piezoelectric oscillator;

acoustoelectrically interacting a transition field formed by a transition region of a piezoelectric resonator with said medium;

establishing frequencies of vibration of said piezoelectric resonator during said acoustoelectric interaction;

determining said electrical properties from a difference in frequency between said frequencies of vibration and said frequencies of oscillation.

8. The method of claim 7 further comprising the step of forming said piezoelectric resonator from quartz.

9. The method of claim 7 further comprising the step of forming said piezoelectric resonator from AT cue quartz.

10. The piezoelectric resonant sensor of claim 1 wherein said first electrode active geometry is ring shaped, said second electrode active geometry is circular, said first electrode active geometry of outside diameter equal to a diameter of said second electrode active geometry.

11. The piezoelectric resonant sensor of claim 10 wherein said piezoelectric material comprises quartz.

12. The piezoelectric resonant sensor of claim 11 wherein said quartz piezoelectric material is AT cut.

* * * * *